US007691420B2

(12) United States Patent
Raederstorff et al.

(10) Patent No.: US 7,691,420 B2
(45) Date of Patent: Apr. 6, 2010

(54) COMPOSITIONS FOR THE TREATMENT AND PREVENTION OF DIABETES MELLITUS

(75) Inventors: Daniel Raederstorff, Flaxlanden (FR); Sandra Renata Teixeira, Brookline, MA (US); Ying Wang Schmidt, Basel (CH); Peter Weber, Müllheim (DE); Swen Wolfram, Waldshut-Tiengen (DE)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/573,222

(22) PCT Filed: Sep. 15, 2004

(86) PCT No.: PCT/EP2004/010283

§ 371 (c)(1), (2), (4) Date: Mar. 23, 2006

(87) PCT Pub. No.: WO2005/027661

PCT Pub. Date: Mar. 31, 2005

(65) Prior Publication Data

US 2007/0042057 A1 Feb. 22, 2007

(30) Foreign Application Priority Data

Sep. 23, 2003 (EP) .................................. 03021447

(51) Int. Cl.
*A61K 35/82* (2006.01)
*A61K 31/35* (2006.01)
*A61K 9/20* (2006.01)
*A61K 9/48* (2006.01)

(52) U.S. Cl. ................... 424/729; 514/456; 514/732; 514/738; 424/451; 424/464

(58) Field of Classification Search .................. None
See application file for complete search history.

(56) References Cited

U.S. PATENT DOCUMENTS

| 4,868,153 | A | | 9/1989 | Allison et al. | |
|---|---|---|---|---|---|
| 5,318,986 | A | * | 6/1994 | Hara et al. | 514/456 |
| 5,536,499 | A | * | 7/1996 | Znaiden et al. | 424/401 |
| 6,299,925 | B1 | * | 10/2001 | Xiong et al. | 426/597 |
| 6,410,061 | B1 | * | 6/2002 | Morre et al. | 424/729 |
| 6,428,818 | B1 | * | 8/2002 | Morre et al. | 424/729 |
| 6,447,814 | B1 | * | 9/2002 | Lee et al. | 424/725 |
| 6,855,346 | B2 | * | 2/2005 | Wu | 424/728 |
| 2002/0076446 | A1 | * | 6/2002 | Wu | 424/551 |
| 2003/0165580 | A1 | * | 9/2003 | Zhao | 424/725 |
| 2004/0081631 | A1 | | 4/2004 | Lee et al. | |

FOREIGN PATENT DOCUMENTS

| CN | 1120953 A | * | 4/1996 |
|---|---|---|---|
| DE | 101 31 057 | | 1/2003 |
| FR | 2 846 239 | | 4/2004 |
| JP | 1 207233 | | 8/1989 |
| JP | 02 243622 | | 9/1990 |
| JP | 05 292885 | | 11/1993 |
| JP | 2003-235503 A | * | 2/2002 |
| WO | WO 95/00157 | | 1/1995 |
| WO | WO 02/00638 A2 | | 1/2002 |
| WO | WO 02/00638 A3 | | 1/2002 |
| WO | WO 02/39822 A2 | | 5/2002 |
| WO | WO 02/072086 A2 | | 9/2002 |
| WO | WO 2004/041257 A2 | | 5/2004 |

OTHER PUBLICATIONS

Ahmad et al., "Green Tea Polyphenols and Cancer: Biologic Mechanisms and Practical Implications," Nutrition Reviews, Mar. 1999, vol. 57, No. 3, 78-83.*
Ko, Wun-Chang, "A newly isolated antispasmodic—butylalidenephthalide," Japanese Journal of Pharmacology, Feb. 1980, vol. 30, No. 1, 85-91.*
Patent Abstracts of Japan, Section C, No. 655, vol. 13, No. 515, p. 70 (1989), English language abstract of JP 1 207233 A (B1 above), 2002.
Derwent Database English language abstract of DE 101 31 057 A (B2 above), WPI Accession No. 2004-110553/200412, 2002.
Derwent Database English language abstract of FR 2 846 239 (B3 above), WPI Accession No. 2004-347634/200432, 2004.
Chong, Z.Z. et al., Effect of di-3-n-butyiphthalide On The Activity Of The Choline Acetyltransferase In Ischemic Brain And Cultured Neurons Subjected To Hypoglycemia/Hypoxia, Chinese Pharmaceutical Journal, vol. 34, No. 8, pp. 519-522 (1999).
Ko, Wun-Chang, "A Newly isolated antispasmodic-butylaidenephthalide", Japanese Journal of Pharmacology, vol. 30, No. 1, pp. 85-91 (Feb. 1980).
Derwent English language abstract of JP 05 292885 (Document B4 above), 1993.
Patent Abstracts of Japan, vol. 0145, No. 62, English language abstract of JP 02 243622 (Document B5 above), 1990.
Shiral and Suzuki, "Effects of simultaneous docosahexaenoic acid and catechin intakes on the plasma and liver lipids in low- and high-fat diet fed mice," *Nutrition Research*, 23, pp. 959-969 (2003).

* cited by examiner

*Primary Examiner*—Christopher R. Tate
(74) *Attorney, Agent, or Firm*—Bryan Cave LLP

(57) ABSTRACT

Compositions comprising a catechin as found in green tea, e.g., epigallocatechin gallate, and ligand which activates the peroxisome proliferatoractivated receptor gamma (PPAR-gamma are useful for the treatment and prevention of diabetes mellitus).

14 Claims, No Drawings

COMPOSITIONS FOR THE TREATMENT AND PREVENTION OF DIABETES MELLITUS

The present invention relates to compositions for the treatment or prevention of diabetes mellitus, or other conditions associated with impaired glucose tolerance such as syndrome X and obesity. More specifically, the present invention relates to compositions comprising a catechin found in green tea, particularly (−) epigallocatechin gallate (hereinafter: EGCG), and a peroxisome proliferator-activated receptor gamma (hereinafter: PPARγ) ligand. In another aspect, the present invention relates to the use of EGCG in the manufacture of a nutraceutical composition for concomitant consumption in the treatment or prevention of diabetes or obesity by administration of a PPARγ ligand. In still another aspect, the invention relates to a method of treatment or prevention of diabetes mellitus, or other conditions associated with impaired glucose tolerance such as syndrome X and obesity wherein an effective amount of a composition comprising EGCG and a PPARγ ligand is administered to an individual in need of such treatment.

The term composition as used herein comprises a mixture of EGCG and a PPARγ ligand, in particular, a nutraceutical composition. The term "nutraceutical" as used herein denotes a usefulness in both the nutritional and pharmaceutical field of application. Thus, nutraceutical compositions can find use as supplement to food and beverages, and as pharmaceutical formulations for enteral or parenteral application which comprise conventional pharmaceutical excipients and auxiliaries and which may be solid formulations such as capsules or tablets, or liquid formulations, such as solutions or suspensions.

The term "EGCG" as used herein comprises (−)-epigallocatechin gallate (EGCG in the narrower sense) and/or one or more derivatives (esterified forms, glycosides, sulphates) thereof, or other catechins found in green tea such as (−) epigallocatechin (EGC), (−) epicatechin-3-gallate (ECG), (−) epicatechin (EC), (+) gallocatechin, and (+) catechin and derivatives thereof. Of primary interest for use in the present invention is (−)-epigallocatechin gallate.

The term "PPARγ" ligand as used herein denotes a compound which activates or modulates the nuclear receptor PPARγ, thereby enhancing insulin sensitivity. The PPARγ ligand may be a full agonist, a partial agonist (selective modulator), or a PPARα/γ dual or panagonist.

Examples of such PPARγ ligands are thiazolidinediones (hereinafter: TZD's), such as Glitazones, e.g., ciglitazone, rosiglitazone and pioglitazone; natural occurring PPARγ ligands, e.g. ligustilide and other phthalide ananalogues as disclosed in European patent application No. 3010804.7 the contents of which is incorporated herein for reference purposes, e.g., (E)-senkyunolide E; senkyunolide C; senkyunolide B; 3-butyl-4,5,6,7-tetrahydro-3,6,7-trihydroxy-1(3H)-isobenzofuranone; 3-butyl-1(3H)-isobenzofuranone; 3-butylphthalide; 3-butylidenephthalide; chuangxinol; ligustilidiol; senkyunolide F; 3-hydroxy-senkyunolide A; angeloylsenkyunolide F; senkyunolide M; 3-hydroxy-8-oxo-senkyunolide A; ligustilide; 6,7-dihydro-(6S,7R)-dihydroxy-ligustilide; 3a,4-dihydro-3-(3-methylbutylidene)-1(3H)-isobenzofuranone; sedanolide; and cnidilide, especially (E)-senkyunolide E, senkyunolide C, ligustilide, sedanolide, and 3-butylidenephthalide; phytanic acid or a polyunsaturated fatty acid (also referred to herein as PUFA) in an esterified (e.g., as triglycerides or ethyl esters) or a free form, particularly an omega-3 polyunsaturated fatty acid such as eicosapentaenoic acid (5,8,11,14,17-eicosapentaenoic acid, EPA) and docosahexaenoic acid (4,7,10,13,16,19-docosahexaenoic acid, DHA), or an omega-6-polyunsaturated fatty acid such as γ-linolenic acid (6,9,12-octadecatrienoic, GLA).

In particular, the methods of the present invention are useful in inhibiting adipocyte differentiation and the associated increased in body weight observed when diabetic subjects are treated with PPARγ ligand. Thus, the present compositions are particularly efficacious for the prevention and treatment of type 2 diabetes in those individuals with mild impaired glucose tolerance (IGT) and/or obesity as well as in patients with established Type 2 diabetes.

Diabetes is a chronic metabolic disease, which is caused by multiple factors and has become a major public health problem. Non-insulin-dependent diabetes mellitus (NIDDM, type 2 diabetes) is the most common form of diabetes mellitus and constitutes >90% of the diagnosed diabetes cases in western countries. The prevalence of Type 2 diabetes mellitus is increasing rapidly, at least in part as a function of obesity. Type 2 diabetes already affects 6% of the western population and it is estimated that by 2010 more than 200 million people will be affected by the disease. Type 2 diabetes mellitus is characterized by an elevated blood glucose concentration or hyperglycemia that results from abnormalities in insulin secretion and insulin action. Numerous complications of diabetes including heart disease, stroke, renal failure, retinopathy, and peripheral neuropathy contribute to the high rate of morbidity and mortality. Therefore, control of glucose homeostasis is critical for the treatment of diabetes.

There is no ideal treatment for type 2 diabetes and none of the available drugs are sufficiently efficacious to restore normal glucose levels alone or in combination therapy as the disease progresses. Diet and exercise are first-line therapies for Type 2 diabetic patients but often pharmacological intervention becomes necessary. The sulfonylureas and biguanides classes of drugs have been widely used for several decades to control blood glucose levels. Sulfonylureas are compounds that stimulate insulin release from the pancreas. However, treatment with sulfonylureas may lead to hypoglycemia and prolonged use results in side effects, particularly desensitization and/or apoptosis of the pancreatic cells resulting in decreased insulin production. Biguanides are compounds that decrease hepatic glucose output, and thus are efficacious in the treatment of hyperglycemia.

PPARγ ligands have been proposed for use in the treatment of hyperglycemia and insulin resistance in patients with Type 2 diabetes. PPARγ is expressed in adipose tissue and plays a pivotal role in the regulation of adipocyte differentiation. In adipose tissue, TZD type of compounds promote adipocyte differentiation. In diabetic patients several weeks of TZD treatment are required to decrease plasma glucose levels. Thus, PPARγ ligands that promote adipocyte differentiation may lead to increased fat accumulation and weight gain. Indeed, PPARγ agonists in addition to their beneficial effects on glucose homeostasis increase fat cell differentiation and body fat accumulation in humans. Therefore, the use of these PPARγ agonists is not optimal in the long-term treatment of type 2 diabetes. Obesity is highly associated with the progression of insulin resistance and any weight gain must be considered unfavorable in the treatment of type 2 diabetes if the increased body weight compromises the positive effects of the treatment.

In accordance with the present invention it has surprisingly been found that the combination of EGCG and PPARγ ligands results in amelioration and/or elimination of the undesirable side effect of PPARγ agonist-induced adipocyte differentiation, which leads to body fat gain. Thus, PPARγ ligands such as TZD's or its pharmacologically active derivatives can be used, in combination with EGCG to treat Type 2 diabetes mellitus and to inhibit/reduce the PPARγ agonist-induced adipogenesis, while maintaining or increasing the glucose lowering effects.

The combination of EGCG and a PPARγ ligand may be administered either in a single unit dosage form or by dosing each component of the combination to the patient separately in individual dosage forms administered together or sequentially. If the combination is administered as two separate compositions the administration of the two active agents occurs in a time frame over which the subject receives the benefit of the combination of both active agents.

The compositions of the invention may be in a form suitable for oral use (for example as tablets, hard or soft capsules, aqueous or oily suspensions, emulsions, dispersible powders or granules, syrups or elixirs). The compositions of the invention may be obtained by conventional procedures using conventional pharmaceutical excipients, well known in the art. Thus, compositions intended for oral use may contain, for example, one or more colouring, sweetening, flavouring and/or preservative agents. EGCG may also be included in a food which may be consumed along side of a standard PPARγ ligand treatment or in combination with a natural PPARγ ligand such as ligustilide and analogues such as 3-Butylphthalide and 3-Butylidenephthalide, phytanic acid or a polyunsaturated fatty acids such as eicosapentaenoic acid (5,8,11,14,17-eicosapentaenoic acid, EPA) and docosahexaenoic acid (4,7,10,13,16,19-docosahexaenoic acid, DHA).

EGCG doses may be from about 0.03 to about 30 mg/kg body weight/day, more particularly from about 0.2 to about 7 mg/kg body weight/day. If EGCG is administered separately in a food or beverage, said food items may contain about 5 mg to about 500 mg EGCG per serving.

PUFA's doses may be from about 0.1 to about 60 mg/kg body weight/day, more particularly from about 0.2 to about 7 mg/kg body weight/day. If PUFA's is administered separately in a food or beverage, said food items may contain about 5 mg to about 1000 mg PUFA's per serving.

Ligustilide doses may be from about 0.01 to about 50 mg/kg body weight/day, more particularly from about 0.1 to about 20 mg/kg body weight/day. If ligustilide is administered separately in a food or beverage, said food items may contain about 5 mg to about 1000 mg ligustilide per serving.

Phytanic acid doses may be from about 0.1 to about 70 mg/kg body weight/day, more particularly from about 0.2 to about 20 mg/kg body weight/day. If Phytanic acid is administered separately in a food or beverage, said food items may contain about 5 mg to about 1000 mg Phytanic acid per serving.

The doses of the PPARγ ligand, for example ciglitazone, rosiglitazone and pioglitazone will be those approved for use by regulatory bodies for example the FDA and may be found in the Orange Book published by the FDA, or otherwise proposed and known to the medical practitioner. Typical dosages are in the range of about 1 to about 1000 mg, especially about 1 mg to about 100 mg, more particularly about 1 mg to about 30 mg for an adult human of about 70 kg body weight. Alternatively, smaller doses may be used as a result of the benefits derived from the combination according to the invention.

The invention is illustrated further by the Examples which follow.

EXAMPLE 1

A. Adipocyte Differentiation: EGCG Combined with Rosiglitazone or with Pioglitazone C3H10T1/2 (obtained from the American Type Culture Collection) were grown to confluence and treated with insulin alone or insulin and Rosiglitazone or Pioglitazone, or combinations thereof with EGCG for 11 days, as shown in Table 1. After the 11-day treatment, the cells were stained with oil red O. This was followed by extraction of the stain for concentration determination. The results are shown in Table 1.

Co-treatment of C3H10T1/2 cells with rosiglitazone and insulin or with pioglitazone and insulin, resulted in a higher differentiation of these cells into adipocytes than insulin alone as represented by a higher amount of oil Red O staining (Table 1). Co-treatment with insulin, rosiglitazone and EGCG or insulin, pioglitazone and EGCG resulted in a reduction of adipocyte differentiation.

TABLE 1

|  | Optical Density |
|---|---|
| Insulin (100 nM) | 0.21 ± 0.02 |
| Insulin (100 nM) + Rosiglitazone (1 × 10$^{-5}$ M) | 0.30 ± 0.01 |
| Insulin (100 nM) + Rosiglitazone (1 × 10$^{-5}$ M) + EGCG (5 × 10$^{-5}$ M) | 0.25 ± 0.01 |
| Insulin (100 nM) + Pioglitazone (2.5 × 10$^{-5}$ M) | 0.27 ± 0.02 |
| Insulin (100 nM) + Pioglitazone (2.5 × 10$^{-5}$ M) + EGCG (5 × 10$^{-5}$ M) | 0.17 ± 0.01 |

The results show that EGCG blocked TZD-induced adipocyte differentiation. Thus, the combination of EGCG and PPARγ ligand allows a pharmacological treatment that prevents progression of type 2 diabetes, while simultaneously minimizing side effects of PPARγ agonists.

B. Adipocyte Differentiation: EGCG Combined with Ligustilide

C3H10T1/2 (obtained from the American Type Culture Collection) were grown to confluence and treated with insulin alone or insulin and ligustilide, or combinations of insulin, ligustilide and EGCG for 11 days, as shown in Table 2. After the 11-day treatment, the cells were stained with oil red O. This was followed by extraction of the stain for concentration determination. The results are shown in Table 2.

Co-treatment of C3H10T1/2 cells with ligustilide and insulin resulted in a higher differentiation of these cells into adipocytes than insulin alone as represented by a higher amount of oil Red O staining. Co-treatment with insulin, ligustilide and several concentrations of EGCG resulted in a dose-dependent reduction of adipocyte differentiation.

TABLE 2

|  | Optical Density |
|---|---|
| Insulin (100 nM) | 0.14 ± 0.01 |
| Insulin (100 nM) + Ligustilide (50 × 10$^{-5}$ M) | 0.26 ± 0.01 |
| Insulin (100 nM) + Ligustilide (50 × 10$^{-5}$ M) + EGCG (1 × 10$^{-5}$ M) | 0.18 ± 0.01 |
| Insulin (100 nM) + Ligustilide (50 × 10$^{-5}$ M) + EGCG (50 × 10$^{-5}$ M) | 0.11 ± 0.01 |

TABLE 2-continued

| | Optical Density |
|---|---|
| Insulin (100 nM) + Ligustilide (50 × $10^{-5}$ M) + EGCG (1 × $10^{-4}$ M) | 0.12 ± 0.01 |

The above results show that EGCG blocked ligustilide-induced adipocyte differentiation. Thus, the combination of EGCG and the PPARγ ligand ligustilide allows a treatment that prevents progression of type 2 diabetes, while simultaneously minimizing side effects of PPARγ ligands.

C. Effects of the Combined Administration of EGCG and the PPARγ Agonist Rosiglitazone in the db/db Mouse Model The efficacy of the combination of EGCG and rosiglitazone as well as of both compounds alone on body weight, adiposity and glucose tolerance was tested in a 4-week study in C57BLKS/J db/db mice (n=10/group). This model of late type 2 diabetes with severe hyperglycemia and obesity is widely used to determine the efficacy of anti-diabetic and anti-obesity compounds.

Male db/db mice were obtained from Jackson Laboratory (Bar Harbor, Me., USA). Adult mice aged 8 weeks were used in the experiment. Mice were housed individually in plastic cages with bedding and allowed free access to standard rodent food and tap water. The animal rooms were controlled for temperature (24° C.), humidity (55%), and light (12-h light-dark cycle). The animals were randomized into four groups. EGCG and rosiglitazone were administered as feed-ad-mix. Corn cellulose (2% of diet) served as a carrier substance for EGCG and rosiglitazone as well as a placebo when used alone. Group 1 received placebo, group 2 received a diet containing 1% of EGCG; group 3 received a diet containing 0.038% of rosiglitazone; and group 4 received a diet containing 1% of EGCG and 0.038% of rosiglitazone. Body weight and food intake were determined over the course of the study. Total adipose tissue weight was determined by NMR. After four weeks of treatment an oral glucose tolerance test was carried out after an overnight fasting period. The blood glucose levels were measured before (fasted state glucose levels) application of an oral glucose load (1 g/kg body weight) and after 15, 30, 45, 60, 90, 120, 150 and 180 minutes. Area under the curve (AUC) was calculated from the resulting blood glucose curves and served as an indicator of glucose tolerance. At the end of the study, fed state levels of glucose, triglycerides and free fatty acids were determined in plasma. All data are expressed as means for animals in each group. There was no difference in food intake between the groups over the study period.

The results are shown in Tables 3, 4 and 5.

Body weight and adipose tissue weight for each treatment group is shown in Table 3. Administration of rosiglitazone significantly increased body weight and adipose tissue weight. Administration of EGCG moderately decreased body weight and adipose tissue weight compared to control mice. Combined administration of EGCG and rosiglitazone totally abolished the increase in body weight and adipose tissue weight induced by rosiglitazone alone. Moreover, the combined administration resulted in a moderate reduction of body weight and adipose tissue weight compared to control mice. This effect was similar to the effect of the administration of EGCG alone.

TABLE 3

Body weight and adipose tissue weight of db/db mice after administration of EGCG, rosiglitazone, and the combination of both compounds for 4 weeks.

| | Body weight (g) | Total adipose tissue weight (g) |
|---|---|---|
| CONTROL | 41.6 | 23.3 |
| Diet containing EGCG | 38.8*# | 20.9*# |
| Diet containing Rosiglitazone | 50.0* | 29.0* |
| Diet containing EGCG + Rosiglitazone | 39.2*# | 21.2*# |

*significantly different from control,
significantly different from rosiglitazone (P values less than 0.05 were considered significant)

Fasted state glucose levels are shown in Table 4.

Fasted state glucose levels were significantly reduced in mice treated with EGCG, rosiglitazone, and the combination of EGCG and rosiglitazone compared to control mice. Area under the curve was significantly reduced in all treatment groups indicating that glucose tolerance was significantly improved by treatment with EGCG, rosiglitazone, and the combination of EGCG and rosiglitazone. Moreover, the combined treatment with EGCG and rosiglitazone led to a significantly improved glucose tolerance as compared to mice treated with either rosiglitazone or EGCG alone.

TABLE 4

Fasted state blood glucose levels and area under the curve (AUC) of an oral glucose tolerance test of db/db mice after administration of EGCG, rosiglitazone, and the combination of both compounds for 4 weeks.

| | Fasted state glucose (mg/dl) | AUC |
|---|---|---|
| CONTROL | 288.8 | 79765.5 |
| Diet containing EGCG | 132.1* | 38353.5* |
| Diet containing Rosiglitazone | 98.0* | 35185.0* |
| Diet containing EGCG + Rosiglitazone | 79.0* | 22971.8*# |

*significantly different from control,
significantly different from rosiglitazone (P values less than 0.05 were considered significant)

Fed state plasma levels of glucose, triglycerides, and free fatty acids are shown in Table 5.

Fed state plasma levels of glucose, triglycerides, and free fatty acids were significantly reduced by treatment with EGCG, rosiglitazone, and the combination of EGCG and rosiglitazone. However, the effects of rosiglitazone were more pronounced compared to the effects of EGCG. The combined treatment with EGCG and rosiglitazone resulted in similar reductions of these parameters compared to treatment with rosiglitazone alone.

The db/db model is widely used to determine the efficacy of anti-diabetic and anti-obesity compounds. As shown in Tables 3, 4 and 5 these mice rapidly develop severe obesity and hyperglycemia. Furthermore, db/db mice respond well to treatment with the PPARγ ligand rosiglitazone, displaying typical beneficial as well as adverse effects similar to human patients treated with rosiglitazone. Beneficial effects are decreased fasted state blood glucose levels, improved plasma levels of triglycerides and free fatty acids, and enhanced glucose tolerance. One of the most important adverse effects is the pronounced increase in body weight and adipose tissue mass. In the human this effect is limiting the compliance of diabetic patients who, in most cases, are already overweight. Furthermore, the increase in adiposity could cause significant secondary health threats. Thus, an adjuvant therapy preserving or enhancing the beneficial effects of treatment with PPARγ agonists and at the same time inhibiting the adverse effects would be of great importance for the success of any anti-diabetic treatment regimen.

TABLE 5

Fed state plasma levels of glucose, triglycerides, and free fatty acids of db/db mice treated with EGCG, rosiglitazone, and the combination of both compounds for 4 weeks.

|  | Glucose (mmol/l) | Triglycerides (mmol/l) | Free fatty acids (mmol/l) |
|---|---|---|---|
| CONTROL | 46.1 | 2.98 | 53.6 |
| Diet containing EGCG | 33.5*# | 1.47* | 38.9*# |
| Diet containing Rosiglitazone | 22.1* | 1.01* | 25.2* |
| Diet containing EGCG + Rosiglitazone | 21.8* | 1.13* | 23.9* |

*significantly different from control,
significantly different from rosiglitazone (P values less than 0.05 were considered significant)

The above results show that EGCG as an adjuvant in the treatment of Type 2 diabetes and obesity with PPARγ ligands unexpectedly inhibits the adverse effects of treatment with the PPARγ ligands rosiglitazone while its beneficial effects were maintained or even enhanced. Namely, adjuvant therapy with EGCG inhibited the increase in body weight and adipose tissue weight due to rosigliatazone treatment. The effects of rosiglitazone on plasma triglyceride and free fatty acid levels were maintained and glucose tolerance was further enhanced by co-administration of EGCG.

EXAMPLE 2

Soft Gelatin Capsule

Soft gelatin capsules are prepared by conventional procedures using ingredients specified below:

Active ingredients: EGCG 300 mg; Rosiglitazone 8 mg

Other ingredients: glycerol, water, gelatine, vegetable oil

EXAMPLE 3

Hard Gelatin Capsule

Hard gelatin capsules are prepared by conventional procedures using ingredients specified below:

Active ingredients: EGCG 150 mg; Rosiglitazone 8 mg

Other ingredients:

Fillers: lactose or cellulose or cellulose derivatives q.s

Lubricant: magnesium sterate if necessary (0.5%)

EXAMPLE 4

Tablet

Tablets are prepared by conventional procedures using ingredients specified below: Active ingredients: EGCG 100 mg; Pioglitazone 15 mg Other ingredients: microcrystalline cellulose, silicon dioxide (SiO2), magnesium stearate, crosscarmellose sodium.

EXAMPLE 5

Soft Drink with 30% juice

I. A Soft Drink Compound is Prepared from the Following Ingredients:

| Juice concentrates and water soluble flavours | |
|---|---|
|  | [g] |
| 1.1 Orange concentrate | |
| 60.3° Brix, 5.15% acidity | 657.99 |
| Lemon concentrate | |
| 43.5° Brix, 32.7% acidity | 95.96 |
| Orange flavour, water soluble | 13.43 |
| Apricot flavour, water soluble | 6.71 |
| Water | 26.46 |
| 1.2 Color | |
| β-Carotene 10% CWS | 0.89 |
| Water | 67.65 |
| 1.3 Acid and Antioxidant | |
| Ascorbic acid | 4.11 |
| Citric acid anhydrous | 0.69 |
| Water | 43.18 |
| 1.4 Stabilizers | |
| Pectin | 0.20 |
| Sodium benzoate | 2.74 |
| Water | 65.60 |
| 1.5 Oil soluble flavours | |
| Orange flavour, oil soluble | 0.34 |
| Orange oil distilled | 0.34 |
| 1.6 Active ingredient | |
| EGCG | 5.0 |

Fruit juice concentrate and water soluble flavours are mixed without incorporation of air. The color is dissolved in deionized water. Ascorbic acid and citric acid is dissolved in water. Sodium benozoate is dissolved in water. The pectin is added under stirring and dissolved while boiling. The solution is cooled down. Orange oil and oil soluble flavours are premixed. The active ingredients as mentioned under 1.6 are dry mixed and then stirred preferably into the fruit juice concentrate mixture (1.1).

In order to prepare the soft drink compound all parts 1.1 to 1.6 are mixed together before homogenising using a TURRAX and then a high-pressure homogenizer ($p_1$=200 bar, $p_2$=50 bar).

II. A Bottling Syrup is Prepared from the Soft Drink Compound from the Following Ingredients:

|  | [g] |
|---|---|
| Softdrink compound | 74.50 |
| Water | 50.00 |
| Sugar syrup 60° Brix | 150.00 |

The ingredients of the bottling syrup are mixed together. The bottling syrup is diluted with water to 1 l of ready to drink beverage for consumption concomitant with administration of a PPARγ ligand.

EXAMPLE 6

Cereal Bread

Active ingredients:

EGCG and one or more additional components selected from PUFA (EPA; DHA; GLA), ligustilide, phytanic acid are incorporated in this food item EGCG: 2-100 mg/per serving PUFA (EPA; DHA, GLA): 5-200 mg/per serving Ligustilide: 2-100 mg/per serving Phytanic acid: 5-200 mg/per serving Typical serving: 50 g

|  | [%] |
|---|---|
| 5 cereal flour | 56.8 |
| Water | 39.8 |
| Yeast | 2.3 |
| Salt | 1.1 |

The yeast is dissolved in a part of the water. All ingredients are mixed together to form a dough. Salt is added at the end of the kneading time. After fermentation, the dough is reworked and divided before a loaf is formed. Before baking, the surface of the loaf is brushed with water and sprinkled with flour.

What is claimed is:

1. A solid unit oral dosage form for effecting glucose tolerance and inhibiting body weight gain or adipose tissue weight gain associated with use of a PPARγ ligand, comprising a catechin found in green tea, and a peroxisome proliferator-activated receptor gamma (PPARγ) ligand selected from the group consisting of thiazolidinediones, ligustilide and phytanic acid, wherein the catechin and the PPARγ ligand are present in glucose lowering amounts.

2. The solid unit oral dosage form according to claim 1 wherein the catechin is (−) epigallocatechin gallate.

3. The solid unit oral dosage form according to claim 2 wherein (−) epigallocatechin gallate is present in an amount of about 10 mg to about 2000 mg.

4. The solid unit oral dosage form according to claim 1 wherein the PPARγ ligand is ligustilide.

5. The solid unit oral dosage form according to claim 1 wherein the PPARγ ligand is in a dosage of from about 1 to about 1000 mg.

6. The solid unit oral dosage form according to claim 1 wherein the catechin is (−) epigallocatechin gallate and (−) epigallocatechin gallate is present in an amount of from about 10 mg to about 2000 mg, and wherein the PPARγ ligand is present in an amount of from about 1 to about 1000 mg.

7. The solid unit oral dosage form according to claim 6 wherein the PPARγ ligand is ligustilide.

8. The solid unit oral dosage form according to claim 6 wherein the (−)-epigallocatechin gallate is present in an amount of about 2000 mg, and PPARγ ligand is present in an amount of about 1000 mg.

9. The solid unit dosage form according to claim 1, wherein the thiazolidinediones are selected from the group consisting of ciglitazone, rosiglitazone, and pioglitazone.

10. A solid unit oral dosage form for effecting glucose tolerance comprising an effective amount of a catechin found in green tea, and of a peroxisome proliferator-activated receptor gamma (PPARγ) ligand selected from the group consisting of thiazolidinediones, ligustilide and phytanic acid, wherein the effective amount of each of the catechin and the PPARγ ligand in combination reduces fasted state glucose concentration and inhibits body weight gain or adipose tissue weight gain associated with use of a PPARγ ligand.

11. The pharmaceutical composition solid unit oral dosage form according to claim 10 wherein the PPARγ ligand is ligustilide.

12. The pharmaceutical composition solid unit oral dosage form according to claim 10 wherein the catechin is (−) epigallocatechin gallate and (−) epigallocatechin gallate is present in an amount of from about 10 mg to about 2000 mg, and wherein the PPARγ ligand is present in an amount of from about 1 to about 1000 mg.

13. The solid unit oral dosage form according to claim 6 wherein the (−)-epigallocatechin gallate is present in an amount of from 100 mg to 300 mg, and the PPARγ ligand is present in an amount of from 8 mg to 100 mg.

14. The solid unit dosage form according to claim 10, wherein the thiazolidinediones are selected from the group consisting of ciglitazone, rosiglitazone, and pioglitazone.

* * * * *